United States Patent
Strebelle et al.

(10) Patent No.: US 6,350,888 B1
(45) Date of Patent: Feb. 26, 2002

(54) METHOD FOR MAKING AN OXIRANE

(75) Inventors: Michel Strebelle, Brussels; Patrick Gilbeau, Braine-le-Comte; Dominique Balthasart, Brussels, all of (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 09/508,731

(22) PCT Filed: Sep. 10, 1998

(86) PCT No.: PCT/EP98/05750

§ 371 Date: May 26, 2000

§ 102(e) Date: May 26, 2000

(87) PCT Pub. No.: WO99/14208

PCT Pub. Date: Mar. 25, 1999

(30) Foreign Application Priority Data

Sep. 18, 1997 (BE) ............................................. 09700756

(51) Int. Cl.⁷ ....................... C07D 301/12; C07D 301/19
(52) U.S. Cl. ........................................ 549/529; 549/531
(58) Field of Search .................................. 549/529, 531

(56) References Cited

U.S. PATENT DOCUMENTS 3,541,114 A * 11/1970 Taylor et al.
4,379,025 A * 4/1983 Yudovich et al.
5,412,122 A * 5/1995 Saxton et al.

FOREIGN PATENT DOCUMENTS

EP 0100119 A1 2/1984

* cited by examiner

Primary Examiner—T. A. Solola
(74) Attorney, Agent, or Firm—Larson & Taylor PLC

(57) ABSTRACT

An epoxide prepared by epoxidation of an olefinic compound by a peroixide compound in liquid medium is separated from the reaction medium by liquid-liquid extraction using an extraction solvent.

7 Claims, No Drawings

METHOD FOR MAKING AN OXIRANE

This application is a 371 of PCT/EP98/05750 filed Sep. 10, 1998.

The present invention relates to a process for making an epoxide, more particularly to a process for separating the constituents of the reaction mixture obtained during the reaction between an olefinic compound and a peroxide compound in a liquid medium containing a diluent.

It is known in practice, in particular from patent application EP-A-100,119, to convert an olefinic compound (i.e. an organic compound containing at least one carbon-carbon double bond) into the corresponding epoxide by reaction with hydrogen peroxide in a liquid medium containing an alcohol. This process makes it possible, for example, to synthesize 1,2-epoxypropane or 1,2-epoxy-3-chloropropane (epichlorohydrin) starting, respectively, from propylene or allyl chloride, according to the following general equation:

In this known process, the epoxide is systematically obtained as a mixture with the alcohol and water. The mixture of reaction products obtained at the epoxidation reactor outlet usually also contains unconverted reactants and possibly also certain impurities from the reactants and various reaction by-products. Separation of the mixture of reaction products into its constituents by distillation has serious drawbacks, since it is observed that, when this mixture is subjected to distillation, an appreciable fraction of the epoxide produced can be degraded by hydrolysis and/or by alcoholysis. Furthermore, other unwanted reactions can also intervene between various constituents of the reaction mixture during the distillation, thus affecting the production efficiency of the process and potentially complicating the production of an epoxide which satisfies the purity requirements. For example, when this known process is applied to the synthesis of epichlorohydrin by reaction between allyl chloride and hydrogen peroxide in methanol, the allyl chloride, which is often used in excess, and the methanol can form, under usual distillation conditions, appreciable amounts of 3-methoxy-1-propene, which can generate 1,2-epoxy-3-methoxypropane by reaction with hydrogen peroxide. Epichlorohydrin and 1,2-epoxy-3-methoxypropane have virtually the same boiling point. Consequently, they cannot readily be separated by distillation.

The subject of the invention is a simple process for making an epoxide by reaction between an olefinic compound and a peroxide compound, which readily gives the epoxide in a more or less pure form, without degradation of an appreciable fraction of the epoxide during the step for separating the constituents of the mixture of reaction products.

Consequently, the invention relates to a process for making an epoxide by reaction between an olefinic compound and a peroxide compound in a liquid medium containing a diluent which is at least partially water-soluble, in which process a mixture of reaction products comprising the epoxide, the diluent and water, and possibly also unconverted reactants, is collected, the said mixture is placed in contact with an extraction solvent so as to obtain two distinct liquid phases, namely, on the one hand, an extract containing at least some of the extraction solvent and at least 10% of the amount of epoxide produced, and, on the other hand, a raffinate containing at least some of the diluent and at least some of the water, and the said extract and the said raffinate are then treated separately by distillation.

The extraction solvent can contain one or more compounds. Advantageously, the extraction solvent used is one which dissolves the epoxide well and in which the diluent is sparingly soluble. Solvents in which water is poorly or not soluble are suitable. One operates usually in the absence of a solvent soluble in water. It can be advantageous to operate in the absence of a salt. Preferably, the extraction solvent used is one which also dissolves the starting olefinic compound well. A particularly preferred extraction solvent is one which is more or less chemically stable and inert with respect to the constituents of the mixture of reaction products under the extraction conditions, as well as in the subsequent distillation step. It is most particularly preferred to work with an extraction solvent whose presence in small amounts in the reaction medium, for example about 5% by weight, has no negative effect on the epoxidation reaction. In certain particularly advantageous cases, it is possible to use the starting olefinic compound itself as extraction solvent. This proves to be particularly effective when the olefinic compound is allyl chloride.

Extraction solvents which give good results are those whose specific weight differs from that of the mixture of reaction products by at least 0.02 g/cm$^3$, in particular by at least 0.04 g/cm$^3$. The best results are obtained when these specific weights differ by at least 0.05 g/cm$^3$.

Extraction solvents whose boiling point differs from that of the epoxide by at least 5° C., in particular by at least 1° C., are usually. The best results are obtained when these boiling points differ by at least 15° C.

Compounds which can be used as extraction solvents in the process according to the invention are aliphatic or cyclic, linear or branched, optionally halogeiated, saturated hydrocarbons containing from 3 to 20 carbon atoms for instance from 3 to 6 or from 10 to 20 carbon atoms. As examples, mention may be made in particular of n-decane, n-tridecane, 1,2,3-trichloro-propane and decalin (decahydronaphthalene). N-decane is suitable.

The extraction solvent can also be chosen from optionally halogenated, unsaturated hydrocarbons. They usually contain from 3 to 20 carbon atoms. Mention may be made, for example, of allyl chloride.

Particularly effective extraction solvents contain at least one compound chosen from o-dichloro-benzene, m-dichlorobenzene, 1,3,5-trimethylbenzene, decalin, o-chlorotoluene, 1,2,3-trichloropropane, allyl chloride, nitrobenzene and n-decane, and mixtures thereof.

Other compounds which can be used as extraction solvents are aromatic hydrocarbons optionally containing alkyl, halo and/or nitrogenous substituents, containing from 6 to 12 carbon atoms. As examples, mention may be made of o-, m- and p-xylenes, 1,3,5-trimethylbenzene, o-, m- and p-dichlorobenzenes, o-, m- and p-chlorotoluenes and nitrobenzene.

It may be advantageous to use a mixture of at least two different solvents. These can be, for example, mixtures of an aromatic hydrocarbon as described above with an aliphatic hydrocarbon as described above. Other mixtures which may be suitable are mixtures of aliphatic hydrocarbons. Mention may be made, for example, of the alkane mixtures sold under the name Isopar® H and characterized by a boiling point range from 175 to 185° C. They can also be mixtures of aromatic hydrocarbons. Mention may be made, for example, of the alkylbenzene mixtures sold under the name Solvesso® 150 and characterized by a boiling point range from 190 to 196° C.

The epoxide prepared by the process according to the invention and present in the mixture of reaction products is an organic compound generally containing from 2 to 20 carbon atoms and containing at least one epoxide group

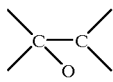

Preferably, it contains from 3 to 10 carbon atoms. It can contain halogen atoms, in particular chlorine. Olefinic compounds which can be used in the process according to the invention generally contain from 2 to 20 carbon atoms. They contain preferably 2, 3 or from 5 to 20 carbon atoms, more particularly 2, 3 or from 5 to 10 carbon atoms, for instance 2 or 3 carbon atoms. Examples of olefinic compounds which can be used in the process according to the invention are propylene, 1-butene, 2-methyl-1-propylene, 3-hexene, 1-octene, 1-decene and allyl chloride. The preferred olefinic compounds are propylene and allyl chloride. Examples of epoxides which can be separated by the process according to the invention are 1,2-epoxypropane, 1,2-epoxybutane, 1,2-epoxy-2-methylpropane, 3,4-epoxy-hexane, 1,2-epoxyoctane, 1,2-epoxydecane and epichlorohydrin. The process according to the invention is particularly suitable for the manufacture of epichlorohydrin. It also gives very good results for the manufacture of 1,2-epoxypropane.

The diluent used in the process according to the invention can be chosen from any organic solvent which is at least partially water-soluble. Alcohols are suitable solvents. The preferred alcohols contain from 1 to 5 carbon atoms and contain only one —OH group. Mention may be made, for example, of methanol, ethanol, n-propanol, isopropanol, butanol and pentanol. The alcohol is usually methanol or tert-butanol.

The peroxide compound used in the process according to the invention can be chosen from hydrogen peroxide and any peroxide compound containing active oxygen and capable of carrying out an epoxidation. Mention may be made, for example, of the peroxide compounds obtained by oxidation of organic compounds such as ethylbenzene, isobutane and isopropanol. Inorganic peroxide compounds are suitable. Hydrogen peroxide is preferred.

The mixture of reaction products generally contains at least 1% by weight of epoxide, usually at least 5% by weight. Typically, it contains not more than 50% by weight, preferably not more than 20%, of epoxide.

The mixture of reaction products generally contains at least 30% by weight of diluent, usually at least 50% by weight. Typically, it contains not more than 90% by weight, preferably not more than 75%, of diluent.

Typically, the mixture of reaction products contains from 5 to 25% of water.

The content of unconverted olefinic compound in the mixture of reaction products is generally from 5 to 20% by weight.

The molar ratio of the amount of olefinic compound used to the amount of peroxide compound used is generally at least 0.5, in particular at least 1. The molar ratio is usually less than or equal to 10, in particular to 4.

The extraction solvent and the mixture of reaction products are placed in contact according to the standard methods of liquid-liquid extraction. Advantageously, an extraction column is used in which the mixture of reaction products is placed in counter-current contact with the extraction solvent.

The temperature at which the extraction solvent and the mixture of reaction products are placed in contact is not critical. It can range from 0 to 80° C. Temperatures above 40° C. are suitable. In practice, it is advantageous to work at the temperature at which the reaction between the olefinic compound and the peroxide compound was carried out.

The extraction solvent and the mixture of reaction products are generally placed in contact at a pressure which can range from atmospheric pressure to a pressure of 30 bar. The pressure is advantageously greater than or equal to 1 bar and less than or equal to 20 bar.

The weight ratio between the extraction solvent and the mixture of reaction products depends on the solvent used and on the extraction apparatus used. In practice, the weight ratio between the extraction solvent and the mixture of reaction products is generally at least equal to 0.1. Preferably, it is greater than or equal to 1. This ratio typically does not exceed 5. Usually, it does not exceed 20. Good results have been obtained with a ratio from 1 to 5.

The subsequent steps for the distillation of the extract and of the raffinate are carried out conventionally and make it possible to collect the epoxide readily in a more or less pure form, to remove water and to recycle the diluent and the unconverted reactants into the step for making the epoxide and the extraction solvent into the step for extracting the mixture of reaction products.

The process according to the invention has proven to be very advantageous for separating 1,2-epoxy-3-chloropropane from the mixtures obtained by reacting allyl chloride with hydrogen peroxide in the presence of a catalyst in a liquid medium containing an alcohol, in particular methanol. It is also suitable for the separation of 1,2-epoxypropane from mixtures obtained by reacting propylene with hydrogen peroxide in the presence of a catalyst. The catalysts suitable in these reactions generally contain a zeolite, i.e. a solid containing silica which presents a crystalline microporous structure. The zeolite is advantageously free from aluminium. It contains preferably titanium. The zeolite can have a crystalline structure of the type ZSM-5, ZSM-11 or MCM-41. The crystalline structures different from beta zeolite are suitable. Zeolites of the ZSM-5 type are particularly suitable. Those presenting an infrared adsorption band at approximately 950–960 cm$^{-1}$ are preferred. Zeolites which are particularly suitable are titanium silicalites. Those corresponding to the formula $xTiO_2(1-x)SiO_2$ in which x is from 0,0001 to 0,5, preferably from 0,001 to 0,05, are performing. Materials of this type, known as TS-1 and presenting a ZSM-5 crystalline structure, give particularly favorable results.

EXAMPLES 1 and 2
(in accordance with the invention)

A mixture of reaction products comprising 67.3% by weight of methanol, 10.0% by weight of allyl chloride, 12.0% by weight of epichlorohydrin and 10.7% by weight of water was used. The specific weight of this mixture was 0.85 kg/l.

Equal volumes of this mixture and of extraction solvent were placed in contact. After extraction (carried out at room temperature and at atmospheric pressure), the concentration of epichlorohydrin in the extract (expressed as g of epichlorohydrin per kg of extraction solvent) and in the raffinate (expressed as g of epichlorohydrin per kg of methanol) were measured. The ratio of these concentrations corresponds to the partition coefficient.

In Example 1, a mixture of saturated aliphatic hydrocarbons, Isopar® H (having a distillation range of 175–185° C. and a specific weight of 0.76 kg/l), was used as extraction solvent. The partition coefficient was 0.20.

In Example 2, decalin was used as extraction solvent. The partition coefficient was 0.21.

EXAMPLES 3 to 8
(in accordance with the invention)

The operations of Example 1 were repeated except for the volumes used. 3 volumes of extraction solvent were placed in contact with 1 volume of reaction product mixture. Various extraction solvents were used (see Table 1, which also indicates the specific weight and the boiling point of the solvents). The partition coefficients obtained are given in Table 1.

TABLE 1

| | | Solvent | | |
|---|---|---|---|---|
| Ex. | Nature | Specific weight | Boiling point | Partition coefficient |
| 3 | 2-chlorotoluene | 1.08 kg/l | 159° C. | 0.61 |
| 4 | nitrobenzene | 1.20 | 211 | 0.57 |
| 5 | 1,2-dichlorobenzene mixture of | 1.30 | 181 | 0.64 |
| 6 | alkylbenzenes Solvesso ® 150 | 0.89 | 190–196 | 0.59 |
| 7 | 1,2,3-trichloropropane | 1.39 | 157 | 1.76 |
| 8 | allyl chloride | 0.94 | 45 | 1.67 |

What is claimed is:

1. A process for making 1,2-epoxy-3-chloropropane by reaction between allyl chloride and an inorganic peroxide compound in a liquid medium containing an alcohol as a diluent, the alcohol being at least partially water-soluble, the process comprising:

collecting a mixture of reaction products comprising 1,2-epoxy-3-chloropropane, the alcohol and water and, optionally, the unconverted reactants;

placing the mixture in contact with an extraction solvent selected from the group consisting of o-xylene, m-xylene, p-xylene, p-dichlorobenzene, o-chlorotoluene, m-chlorotoluene, p-chlorotoluene, n-tridecane, o-dichlorobenzene, m-dichlorobenzene, 1,3,5-trimethylbenzene, decalin, o-chlorotoluene, 1,2,3-trichloropropane, allyl chloride, nitrobenzene and n-decane, and mixtures thereof, so as to obtain two distinct liquid phases, said extraction solvent being suitable for dissolving 1,2-epoxy-3-chloropropane, the alcohol being sparingly soluble in the solvent, the liquid phases comprising an extract containing at least some of the extraction solvent and at least 10% of the amount of 1,2-epoxy-3-chloropropane produced, and a raffinate containing at least some of the alcohol and at least some of the water;

collecting separately the extract and the raffinate;

subjecting the extract to a distillation in order to remove 1,2-epoxy-3-chloropropane therefrom; and subjecting the raffinate to a distillation in order to remove water therefrom.

2. The process according to claim 1, wherein the density of the extraction solvent differs from that of the mixture of reaction products by at least 0.04 g/cm$^3$.

3. The process according to claim 1 wherein the boiling point of the extraction solvent differs from that of 1,2-epoxy-3-chloropropane by at least 5° C.

4. The process according to claim 1 wherein the mixture of reaction products is placed in counter-current contact with the extraction solvent in a liquid-liquid extraction column, at a temperature of from 0 to 80° C.

5. The process according to claim 1, wherein the weight ratio between the extraction solvent and the mixture of reaction products is at least equal to 0.1 and does not exceed 20.

6. The process according to claim 1, wherein the alcohol and the unconverted reactants, collected during the distillation, are returned to the step for making 1,2-epoxy-3-chloropropane.

7. The process according to claim 1 wherein the peroxide compound comprises hydrogen peroxide.

* * * * *